United States Patent [19]
Khan et al.

[11] Patent Number: 5,105,655
[45] Date of Patent: Apr. 21, 1992

[54] RHEOLOGICAL DEVICE FOR IN SITU MEASUREMENTS OF PHOTO POLYMERIZATION KINETICS

[75] Inventors: Saad A. Khan, Howell; Gabor D. Kiss, Long Valley, both of N.J.; Kirk J. Mikkelsen, Chanhassen, Minn.

[73] Assignee: Bell Communications Research, Inc., Livingston, N.J.

[21] Appl. No.: 643,464

[22] Filed: Jan. 18, 1991

[51] Int. Cl.$^5$ ............................................. G01N 11/00
[52] U.S. Cl. .................................................... 73/60
[58] Field of Search ...................... 73/54, 60, 866, 843

[56] References Cited

U.S. PATENT DOCUMENTS

| | | | |
|---|---|---|---|
| 3,740,126 | 6/1973 | Goto | 352/69 |
| 4,494,148 | 1/1985 | Svatek | 358/226 |
| 4,546,438 | 10/1985 | Prewitt et al. | 364/473 |
| 4,566,324 | 1/1986 | Vinogradov et al. | 73/60 |
| 4,601,195 | 7/1986 | Garritano | 73/60 |
| 4,602,502 | 7/1986 | Joseph et al. | 73/60 |
| 4,633,708 | 1/1987 | Blommaert | 73/59 |
| 4,760,734 | 8/1988 | Maxwell | 73/60 |
| 4,779,452 | 10/1988 | Cohen-Tenoudji et al. | 73/54 |
| 4,794,788 | 1/1989 | Masters et al. | 73/59 |
| 4,817,416 | 4/1989 | Blanch et al. | 73/55 |
| 4,876,690 | 10/1989 | Nishida et al. | 372/34 |
| 4,878,379 | 11/1989 | Deer | 73/60 |
| 4,905,504 | 3/1990 | Carriere et al. | 73/60 |

*Primary Examiner*—Robert Raevis
*Attorney, Agent, or Firm*—Leonard C. Suchyta; Lionel N. White

[57] ABSTRACT

A rheological device suitable for measuring the rate of polymerization of ultraviolet sensitive polymers includes a part of open-ended cylindrical fixtures having removable quartz windows at one end. The upper fixture is adapted with a window which permits light to enter and impinge upon the surface of an elliptically-shaped mirror. Curing is monitored by measuring the elastic and viscous moduli during polymerization.

7 Claims, 2 Drawing Sheets

RHEOLOGICAL DEVICE FOR IN SITU MEASUREMENTS OF PHOTO POLYMERIZATION KINETICS

FIELD OF THE INVENTION

This invention relates to a rheolgoical device. More particularly, the present invention relates to a rheolgoical device designed for measuring, in situ, the rate of polymerization of ultraviolet sensitive polymers.

Ultraviolet radiation curable polymers are currently being used in optoelectronic applications, as for example, in coatings and splices for optical fibers. The effectiveness of these materials in providing mechanical reliability depends, in large measure, on the degree of curing of the polymer. A typical technique, of high sensitivity, for evaluating changes in polymer proprieties during the curing process involves the use of a rheolgoical technique in which the time dependent modulus of the material is measured. Unfortunately, an in situ technique for monitoring the rate of curing of UV sensitive polymers has not been available. In accordance with the present invention, this prior art limitation has been effectively obviated by means of a novel rheometric device which when used in conjunction with a mechanical spectrometer serves as a monitoring means during in situ curing.

The invention will be more readily understood by reference to the following detailed description taken in conjunction with the accompanying drawing wherein:

DETAILED DESCRIPTION

Figure 1:
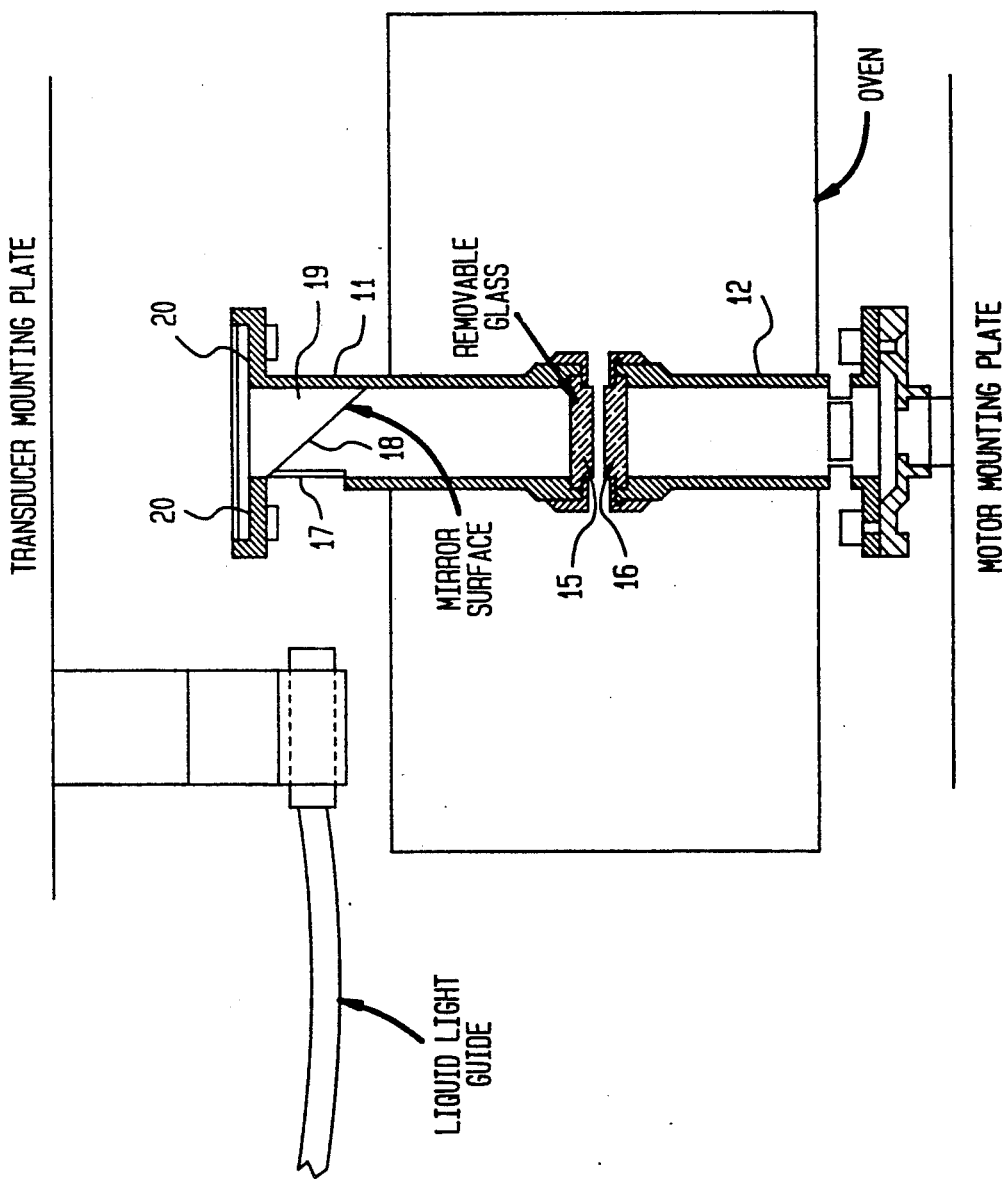
Figure 2:
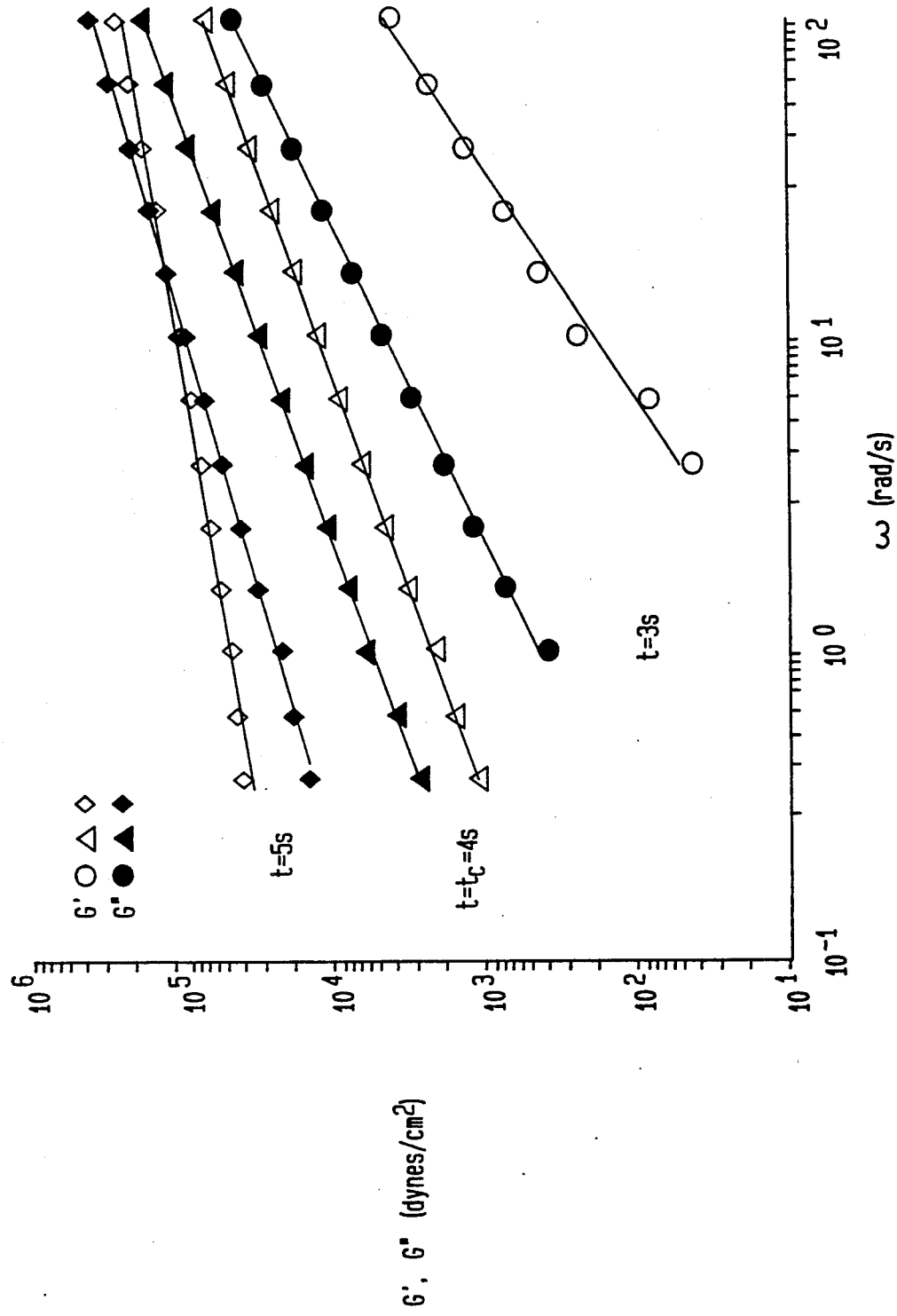

FIG. 1 is a front elevational view in cross-section of the rheometric device of the invention, and FIG. 2 is a graphical representation on coordinates of frequency in radians per second against modulus in dynes per square centimeter comparing the elastic modulus and viscous or loss modulus of a UV irradiated polymer sample at varying exposure times.

With reference now to FIG. 1, there is shown a front elevational view, in cross-section of the rheometric device of the invention. Shown in the FIG. are a pair of open-ended cylindrical fixtures 11 and 12 adapted with removable quartz circular windows 15 and 16, respectively, at one end thereof. Fixture 11 also includes window 17 which permits light to enter the fixture and impinge upon elliptically-shaped mirror 18 having a UV reflective coating ad which is disposed at a 45 degree angle to the plane of windows 15 and 16, mirror 18 being glued to the surface of a removable cylindrical block 19 which may slide in and out of fixture 11, block 19 being held in place by recess 20. Removable quartz disks 15 and 16 are affixed to the adjacent ends of fixtures 11 and 12. The interior walls of fixtures 11 and 12 are mat dull in nature to prevent reflection from side walls during operation of the device.

In operation, the rheometric device of the invention is connected at its lower end to a motor and to a transducer at the opposite end. The resultant assembly is positioned such that the window 17 is above the top surface of an oven. Curing of a polymeric material may then be effected. To this end, a polymer sample is positioned between quartz disks 15 and 16, and the sample exposed to ultraviolet radiation The UV beam exposure time of the sample can be controlled by means of a shutter. Typically, the ultraviolet light source is an Oriel mercury lamp. Light from this source is passed through a water filter, an interference filter which permits passage of a 365 nm wavelength (or any other desired wavelength), a condensing lens and finally through a liquid light guide. An electronic shutter may be placed in the optical train immediately after the water filter. The end of the light guide, which is adapted with a focusing lens, is attached to the base plate of a rheometer which holds the transducer. Since sample thickness is varied by moving this plate, the light guide does not have to be adjusted for different sample thicknesses. During exposure, the sample is uniformly irradiated over its cross section, so assuring uniform polymerization.

Curing of the sample may then be monitored by exposing the sample to a UV beam for a known period of time. Following the exposure, the elastic (G') and viscous (G") moduli of the sample are measured as a function of the shear frequency. In view of the fact that the moduli are extremely sensitive to the degree of cross-linking in the sample, changes may be observed during the curing sequence.

With reference now to FIG. 2, there is shown a graphical representation on coordinates of radians per second against modulus in dynes/cm$^2$ showing the elastic and viscous modulus of a commercially available UV irradiated curable optical adhesive at varying times of exposure. The moduli are observed after 3, 4, and 5 second exposures. It will be noted that at 3 seconds exposure, the elastic and viscous moduli have differing slopes with the viscous modulus being significantly larger. However, at 4 seconds exposure the moduli have the same slope for all frequencies, so indicating that the critical gel point has been attained. At 5 seconds exposure the elastic modulus becomes flatter and is greater than the viscous modulus up to frequencies of approximately 20 radians per second. This corresponds to a post-gel state.

The use of the rheometric device described permits monitoring the material properties of a UV curable polymer during polymerization as the material moves through changes of state from a liquid through the gel point to a solid. Accordingly, the worker is able to ascertain the strength of the material as a function of UV dosage, so enabling one to determine the time period required to cure a splice or coating to meet specific requirements or to determine the effect of sample thickness and temperature on curing. Additionally, one may determine if there is any dark cure following cessation of UV radiation with time.

What is claimed is:

1. In a mechanical spectrometer for measuring rheolgoical properties of a sample material and comprising upper and lower members fixedly mounted on a common vertical rotation axis to transducer means and rotational drive means, respectively, and providing at their respective lower and upper ends opposed substantially parallel contact surfaces arranged perpendicular to said rotation axis to engage said sample material therebetween, the improvement which comprises means for initiating, in situ, the polymerization of a light-sensitive polymer sample material and wherein:

a) said upper member comprises a hollow cylindrical fixture mounted with its longitudinal axis substantially coincident with said rotation axis;

b) said upper contact surface comprises the lower surface of a transparent window element affixed across the lower open end of said fixture;

c) a mirrored surface is mounted within said fixture at substantially a 45 degree angle to and at the intersection of said longitudinal axis and an intersecting transverse axis;
d) said fixture further comprises a window in the portion of the cylindrical wall thereof that is on said transverse axis and facing said mirrored surface; and
e) illuminating means is fixedly mounted with respect to said wall window and is arranged to project light therethrough along said transverse axis to incidence upon said mirrored surface, whereby a light-sensitive polymer sample situated between said contact surfaces may be irradiated for in situ curing during a rheolgoical measurement procedure.

2. Improvement in accordance with claim 1 wherein the interior wall of said fixture is mat dull.

3. Improvement in accordance with claim 1 wherein said contact surface window is a removable quartz disk.

4. Improvement in accordance with claim 1 wherein said mirrored surface is UV reflective.

5. Improvement in accordance with claim 1 wherein:
a) said lower member comprises a second hollow cylindrical fixture mounted with its longitudinal axis substantially coincident with said rotation axis; and
b) said lower contact surface comprises the upper surface of a transparent window element affixed across the upper open end of said second fixture.

6. Improvement in accordance with claim 5 wherein said lower contact surface is a removable quartz disk.

7. Improvement in accordance with claim 6 wherein the interior wall of said second fixture is mat dull.

* * * * *